United States Patent [19]

Glassman

[11] 4,265,245
[45] May 5, 1981

[54] DOUBLE-DUTY DIAPER

[76] Inventor: Jacob A. Glassman, 1680 Michigan Ave., Miami Beach, Fla. 33139

[21] Appl. No.: 21,352

[22] Filed: Mar. 19, 1979

[51] Int. Cl.³ .............................................. A41B 13/02
[52] U.S. Cl. ...................................................... 128/287
[58] Field of Search ................................ 128/284, 287

[56] References Cited

U.S. PATENT DOCUMENTS

| | | | |
|---|---|---|---|
| 3,402,715 | 9/1968 | Liloia et al. .......................... | 128/287 |
| 3,636,952 | 1/1972 | George ................................. | 128/287 |
| 3,863,637 | 2/1975 | MacDonald et al. ................ | 128/287 |
| 4,019,517 | 4/1977 | Glassman ............................. | 128/284 |
| 4,022,210 | 5/1977 | Glassman ............................. | 128/284 |
| 4,072,150 | 2/1978 | Glassman ............................. | 128/287 |
| 4,084,592 | 4/1978 | Tritsch ................................. | 128/287 |

Primary Examiner—C. Fred Rosenbaum
Attorney, Agent, or Firm—Elmer L. Zwickel

[57] ABSTRACT

A double-duty diaper comprising a main diaper having an outer layer of water impervious material and a body contacting inner layer of moisture absorbent material and including a removable insert strip arranged on the body contacting surface of the main diaper capable of absorbing moisture and retaining loose excrement. The insert strip includes moisture proof means manipulatable to prevent lateral overflow of moisture and excrement prior to and during removal of the soiled insert strip from the main diaper. The main diaper is such that it can be used without the insert and it also includes means to cover wastes therein while being removed from the body.

11 Claims, 17 Drawing Figures

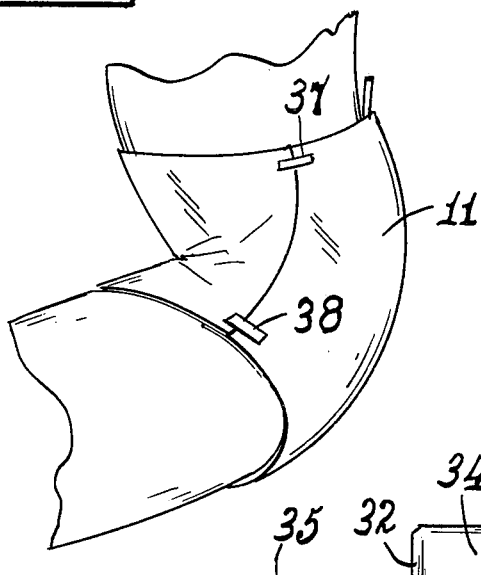
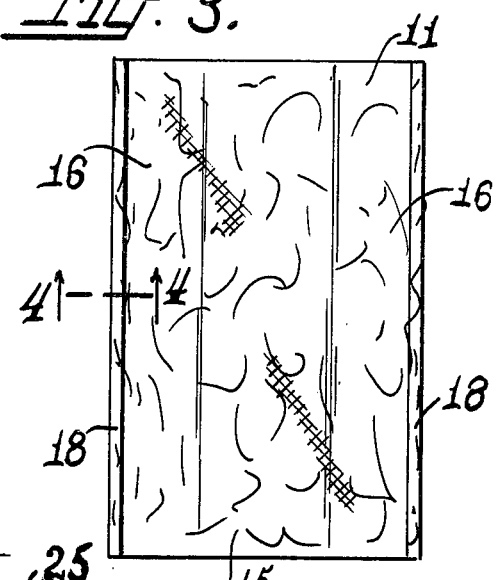
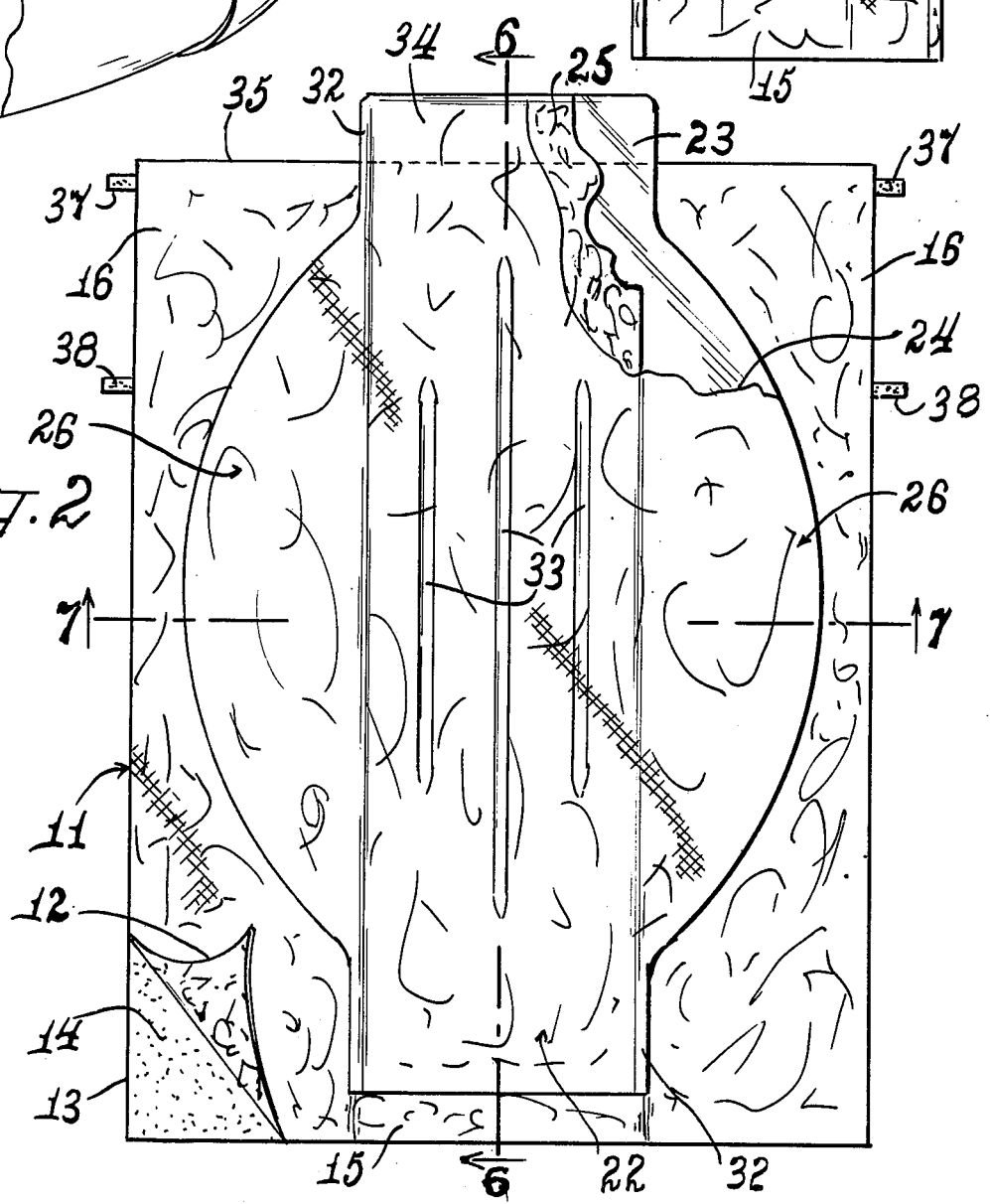

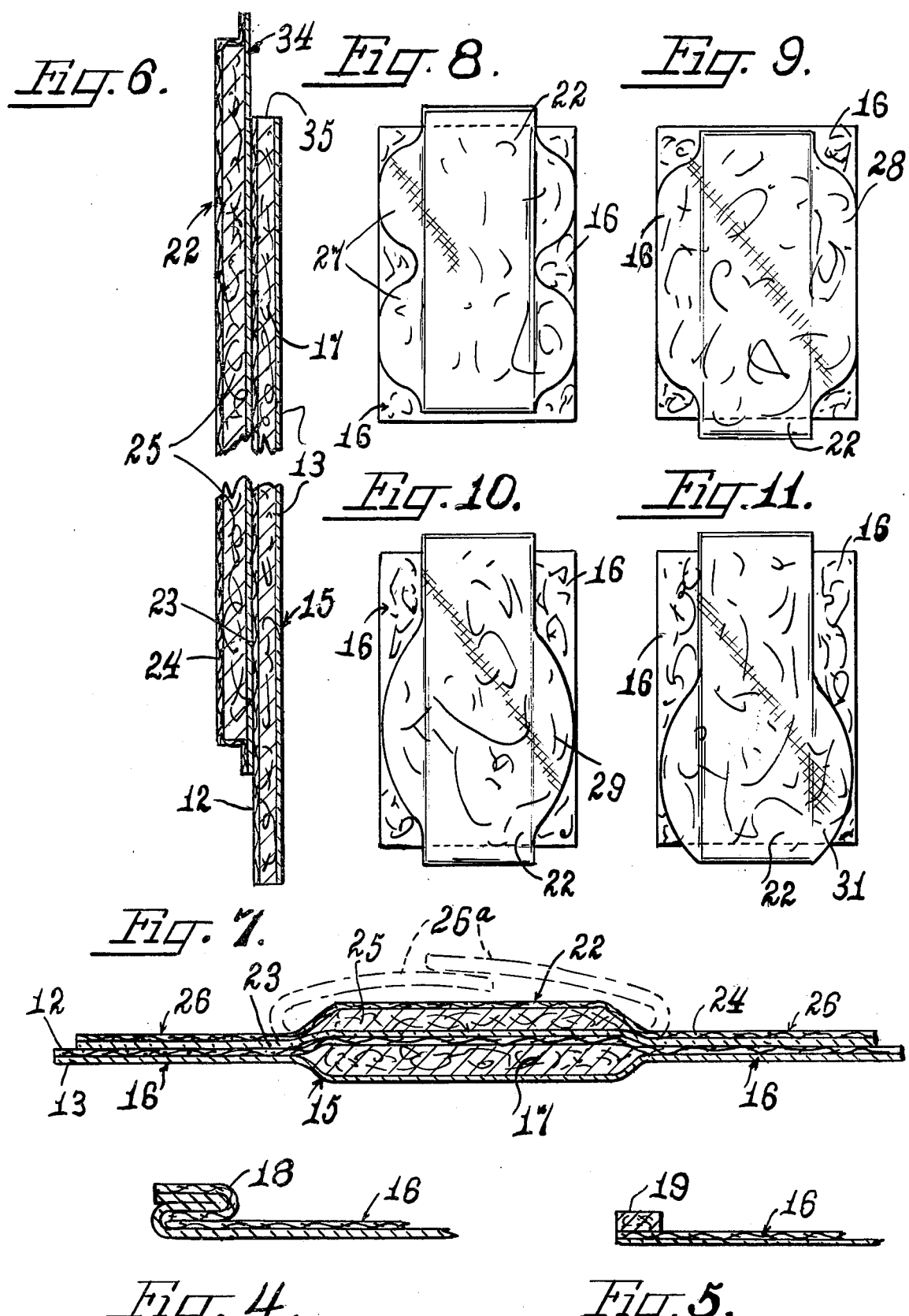

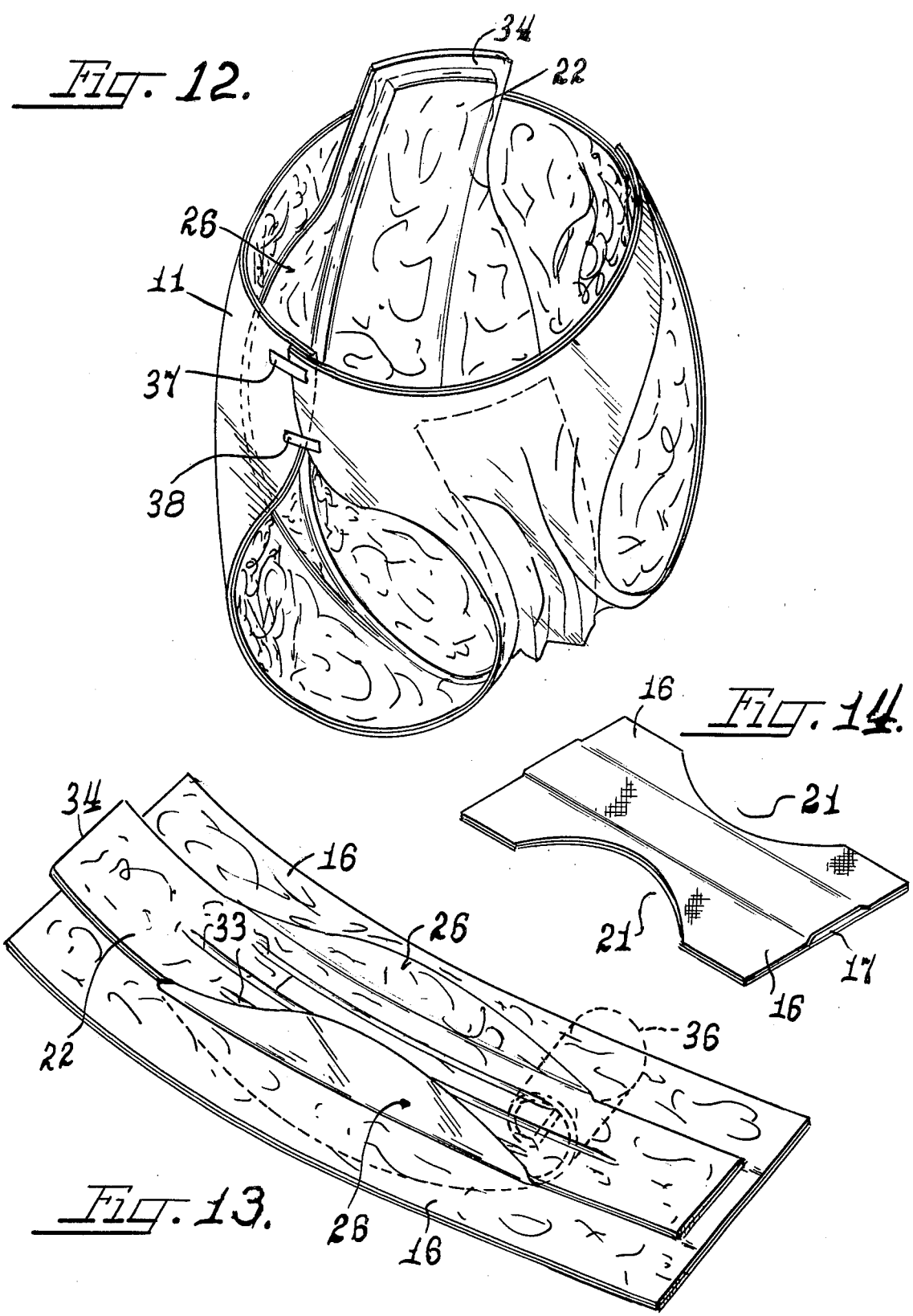

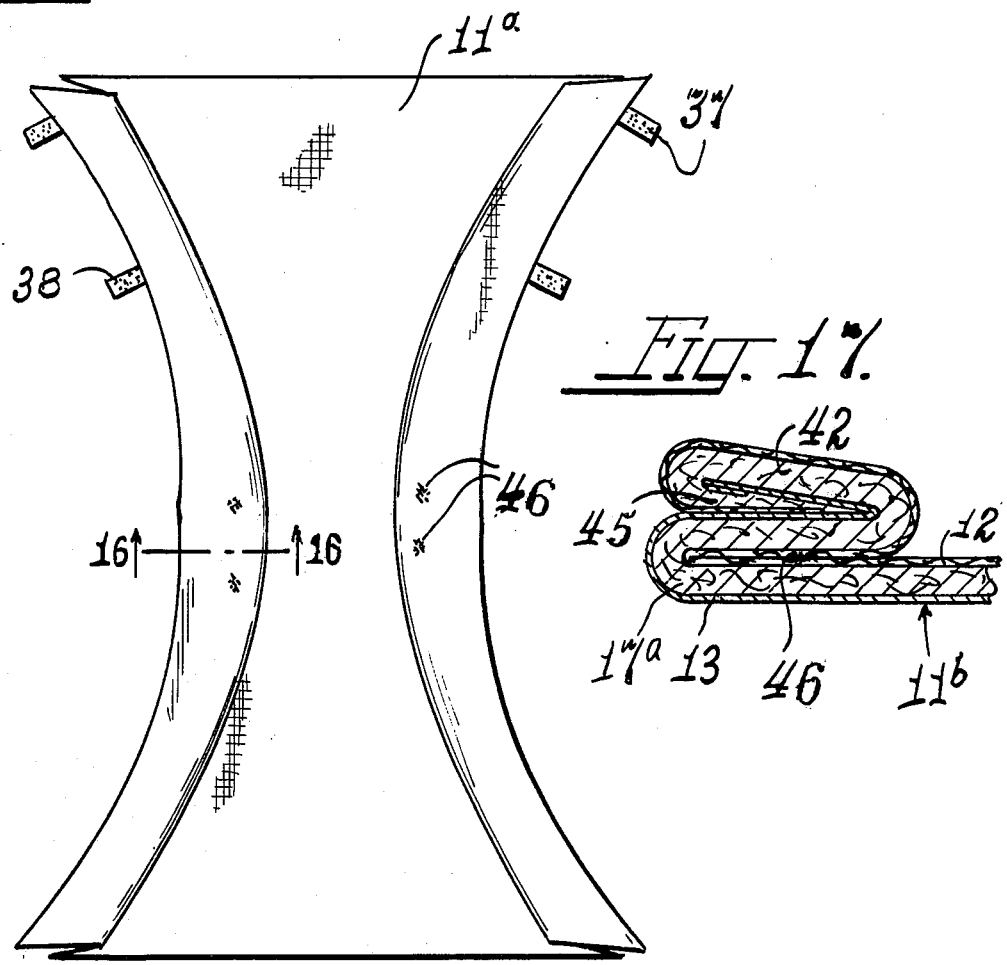
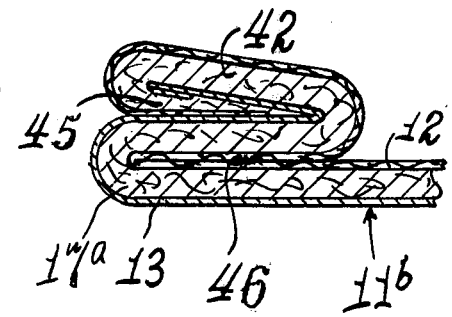
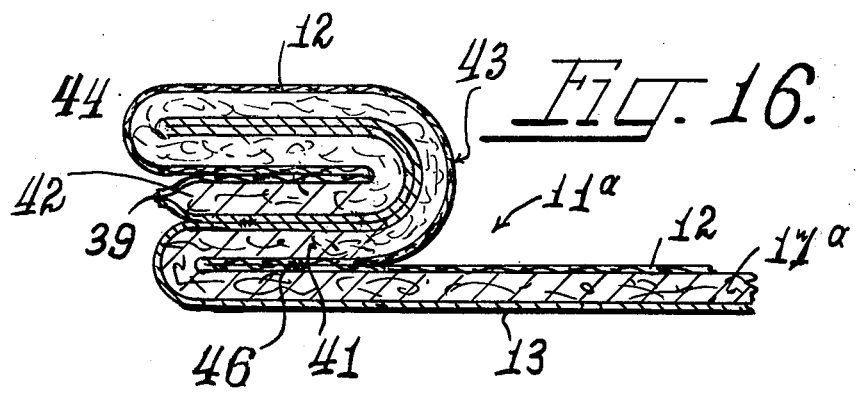

DOUBLE-DUTY DIAPER

The invention relates to improvements in the type of double-duty diaper generally disclosed and claimed in my U.S. Pat. No. 4,072,110, issued Feb. 7, 1978, entitled "Double-Duty Diaper and Insert Therefor". As disclosed in the aforesaid patent the double-duty diaper comprises essentially a main diaper and a removable insert strip, the insert strip being designed to initially accumulate moisture and waste and thereupon be removed from the main diaper without detracting from the effectiveness of the diapering potential of the main diaper. It has been experienced that upon certain occasions of excessive moisture or liquid feces there is a spill-over from the insert strip laterally onto the main diaper thus soiling the latter and rendering it ineffective for further use.

This problem is overcome by providing a moisture absorbing insert strip with what might be termed "lateral wings" that are resistant to moisture penetration and are capable of being folded inwardly laterally over the top of a soiled insert strip prior to said insert strip being withdrawn from the main diaper. In this manner, the soiled area of the insert strip is covered so as to retain any excessive waste matter, fluid or otherwise, and prevent soiling of the hands and/or main diaper during removal of the insert strip. Further, during removal, the insert strip can be rolled up end to end thus affording further protection against loss of its contents. The main diaper is constructed much in the manner of the insert strip except that it has wide lateral moisture resistant areas extending on either side of a relatively narrow central portion of moisture absorbing material. This results in a considerable saving in material cost.

Accordingly, it is an object of the invention to provide a main diaper with a removable insert strip having means to prevent spill-over and avoid possible soiling of the main diaper.

Another object of the invention is to provide a diaper insert strip with means to facilitate its removal from the diaper when soiled without loss of any of its contents.

Another object of the invention is to provide a diaper insert strip that has a moisture impervious back sheet extending laterally from a central absorbent portion and adapted to be folded inwardly laterally to cover the soiled absorbent front face of its central absorbent portion.

Another object is to provide a disposable diaper having novel means to resist leakage around the wearer's thighs.

Another object is to provide an insert strip for a diaper assembly that is sealed about its perimeter and has moisture impervious lateral wings.

Another object is to provide a diaper insert strip with novel means to facilitate wide distribution of moisture without spill-over, and to provide maximum means for containing such moisture in the insert strip prior to and during removal of the insert strip from the main diaper.

Other objects and advantages of the invention will become apparent with reference to the following description and accompanying drawings:

In the drawings:

FIG. 1, is a side view of an improved diaper fitted onto an infant, showing the manner of securing the areas surrounding the thighs against leakage.

FIG. 2 is a plan view of the body contacting surface of one embodiment of the double-duty diaper, showing parts broken away.

FIG. 3 is a top plan view of a diaper having thigh embracing relatively thick longitudinal margins.

FIG. 4 is a detail sectional view of one margin of the diaper shown in FIG. 3, taken substantially on line 4—4 of FIG. 3.

FIG. 5 is a view similar to FIG. 4, showing a modified margin structure.

FIG. 6 is a longitudinal sectional view of the diaper and insert strip, taken substantially on line 6—6 of FIG. 2.

FIG. 7 is a lateral sectional view of the diaper and insert strip, taken substantially on line 7—7 of FIG. 2.

FIGS. 8–11 are views similar to FIG. 2, but on reduced scale, showing veriations in the insert strip structure.

FIG. 12 is a perspective view of the diaper, illustrating the relative position of the insert strip during use.

FIG. 13, is a perspective view of the insert strip and diaper, showing one of the lateral wings on the insert strip folded over the central region of the insert strip.

FIG. 14 is a view on reduced scale, of the improved diaper having lateral thigh notches.

FIG. 15 is a plan view of the top face of a diaper folded along its longitudinal margins to effectively thicken the diaper at its edges so as to snugly embrace the wearer's thighs to resist leakage.

FIG. 16 is an enlarged sectional view of one edge of the diaper shown in FIG. 15, taken substantially on line 16—16 of FIG. 15.

FIG. 17 is a view similar to FIG. 16, but illustrating a slightly modified structure.

Referring to the disclosures in the accompanying drawings, there is disclosed a number of modifications, all of which are basically similar. For example, FIGS. 8–11 shown double-duty diapers that vary from the one shown in FIG. 2, only in the configuration and disposition of the lateral wings on the insert. Accordingly, the following description will pertain to the FIG. 2 embodiment with specific reference to FIGS. 8–11 when variation is present. The main diaper depicted in FIG. 3 responds to the FIG. 2 main diaper except that the longitudinal edges of the main diaper are thickened for purposes of restricting the escape of wastes arount the wearer's thighs; and FIG. 14, which depicts longitudinal notched edges for a purpose of minimizing wrinkling as will be presently noted.

In the FIGS. 2, 6 and 7 disclosures, the double-duty diaper includes a main diaper 11 comprising a thin layer of moisture pervious material 12, such as cotton, cellulose, Crim, or non-woven fluff, having a thin outside layer or backing sheet 13 of moisture impervious material, such as vinyl. These two layers are of like size, have a rectangular shape and, preferably are secured together throughout their contacting surfaces, or at least along their complemental longitudinal edges, as by fusing or an adhesive 14, to form a substantially rectangular main diaper having a longitudinal central portion or area 15 and adjacent relatively wide side marginal areas 16. The central area 15 has a relatively thick layer 17 (FIG. 7) of moisture absorbent material such as cotton, cellulose, crim or non-woven fluff, arranged between layers 12-13 to constitute the main moisture absorption portion of the main diaper. If desired, the longitudinal edges of the side marginal areas 16 may carry an added thickness of absorbent material, such as is shown at 18 and 19 in FIGS. 3, 4 and 5 to provide a snug fit about the thighs of the wearer; or they may be centrally cut away, as at 21 in FIG. 14, to more snuggly fit the thighs with minimum wrinkling.

An auxiliary insert strip 22 (FIG. 2) comprised of a thin bottom layer 23 of plastic sheet material, a relatively thin top layer 24 of highly moisture absorbent material, such as cotton, cellulose, crim, or non-woven fluff, and an intermediate thick layer 25 of absorbent material. The plastic bottom layer 23 and the top absorbent layer 24 are, in part, wider than the thick absorbent layer 25 so as to define, on each side of layer 25, a lateral wing 26. The two material layers 23–24 constituting the wings 26 are adhesively secured together, face to face, and these wings may have a semi-circular outline, as shown in FIG. 2, or they may be located and shaped as per wings 27, 28, 29, and 31, shown in FIGS. 8–11, respectively. At any event, the wings should be no wider than the width of the lateral extensions. The marginal edges of the thick layer 25, at least one of which extends beyond the related end edges of wings 26, are enclosed and sealed against moisture spill-over by sealing the protruding margins of the top and bottom layer 23–24 together face to face.

The body contacting face of the layers 23–24 preferably are formed with companion longitudinal grooves 33 which function to assist distribution of moisture longitudinally of the insert strip. The insert strip is disposed with its plastic bottom face 23 over and against the absorbent face 12 of the main diaper 11 preferably with one of its ends 34 (FIG. 2) extending beyond the complemental end edge 35 of the main diaper 11 so as to afford a projecting tab or the like for grasping the insert strip and withdrawing it from the main diaper when soiled. The insert strip is normally retained in place on the main diaper by a rupturable adhesive.

Prior to withdrawal of a soiled insert strip it is preferable particularly when the diaper insert strip has been excessively wetted or soiled by loose feces, to infold the lateral wings 26, as indicated by 26a in FIG. 7. Furthermore, either end of the insert strip can be folded or rolled longitudinally inwardly during withdrawal as illustrated by dotted lines 36 in FIG. 13.

The full diaper 11a shown in FIGS. 15–17, can be used alone or it can have an auxiliary insert strip 22 associated with it. This diaper is comprised of a thin bottom layer 13 of moisture impervious material upon which is arranged a mass of moisture absorbent material 17a, which may be cotton, cellulose, crim or non-woven fluff. The top of the absorbent material 17a is covered with a thin layer 12 of non-woven fluff or the like, and the two layers have their edges joined by an adhesive, as at 39. As best illustrated in FIG. 16, the longitudinal edges of the diaper 11a are folded over inwardly upon itself to provide a marginal layer 41, then outwardly to provide layer 42. The two folded over thicknesses 41–42 are again folded as at 43 to provide a double thickness top layer 44. The thick marginal areas insure a snug fit about the thighs of the wearer and prevent spill-over. The manner of folding insures that the layers 12 and 17a of absorbent material are always on the body facing side of the diaper.

The diaper 11b illustrated in FIG. 17 is similar to the FIG. 16 disclosure and like numerals represent like parts. Here, the marginal edge 45 of the diaper is tucked beneath the folded layer 42 to present a more "finished" edge to the diaper. In both FIG. 15 and 17 disclosures, a small quantity of rupturable adhesive 46 retains the folds in place. Preferably, either or all layers 12, 17, 17a, 24 and 15 of absorbent material may be treated with a highly absorbent starch to increase their absorbent rate. A starch such as Polimer 35-A-100, distributed by Great Grain Processing Corp., is preferred.

The diapers herein disclosed can, of course, be secured about the body of a child by use of ordinary pins; but preferably,, adhesive coated tabs 37 are provided. Also, in order to minimize seepage about the thighs of the child, the free edges of the fitted diaper can be manually drawn relatively snug about the thighs and then held in place by adhesive coated tabs 38.

When the absorbent layer 25 of the insert strip 22 becomes wetted or soiled, the attendant may fold the wings 26 over the soiled area and then grasp the exposed pull tab 34 of said strip and by the application of a slight tug can separate said insert strip from the main diaper 11 and withdraw said strip. As a consequence, the clean unsoiled or non-wetted main diaper remains in place and in effect constitutes a clean diaper. Thus, the diaper is in effect a double-duty diaper, the need to change frequently is cut in half and the wearer is undisturbed by the withdrawal of the insert strip. This is particularly advantageous when the wearer is sleeping.

Although I have described preferred embodiments of the invention in considerable detail, it will be understood that the description thereof is intended to be illustrative rather than restrictive, as details of the structure and method of fabrication may be modified or changed without departing from the spirit or scope of the invention.

I claim:

1. A double-duty diaper comprising, in combination, a main diaper including at least one relatively thick substantially rectangular layer of highly moisture absorbent material constituting a longitudinal central portion, a thin layer of moisture impervious material underlying the central portion and extending laterally beyond the longitudinal edges of said central portion, a thin layer of moisture pervious material overlying the central portion and having laterally extending side portions one overlying each lateral extension of the moisture impervious material, said lateral extensions each having a width corresponding at least to one-half the width of the longitudinal central portion and being bonded together face to face; and a removable body contacting insert strip including a central relatively thick body of highly moisture absorbent material of a width responding substantially to the width of and superposed on the said longitudinal central portion, adhesive means removably securing the insert strip to said central portion, and means to prevent spillover from said insert strip onto the main diaper comprising thinner lateral wing portions on said central relatively thick body each terminating short of the ends of said thick body and being of a width not greater than the width of the laterally extending side portions of the main diaper, said thinner wing portions comprising a thin bottom layer of moisture impervious material and a thin upper layer of moisture absorbing material bonded together face to face.

2. The double duty diaper recited in claim 1, wherein the insert strip is longer than the main diaper and has at least one end projecting outwardly beyond the complemental end of the main diaper to define a tab to facilitate endwise removal of the insert strip from the main diaper without corresponding removal or impairment of the diapering potential of the main diaper.

3. The double-duty diaper recited in claim 1, wherein at least the insert strip has a series of longitudinal grooves on its wearer-facing surface to facilitate distribution of moisture.

4. The double-duty diaper recited in claim 1, wherein only the insert strip has a series of longitudinal grooves on its wearer-facing surface to facilitate distribution of moisture.

5. The method of fabricating a double-duty diaper comprising the steps of providing a main diaper with a thick layer of highly moisture absorbent material along its longitudinal center, providing an insert strip including a relatively thick layer of highly moisture absorbent material and an underlying layer of moisture impervious material, sealing the perimeter edges of the strip to resist moisture spill-over, positioning said insert strip on said central portion so that at least a portion of the insert strip projects beyond a related end edge of said thick layer to facilitate withdrawal of the insert strip from the main diaper, and providing laterally extending side portions on the insert strip to provide wings to be folded over the insert strip when the latter is soiled.

6. The method recited in claim 5, with the added step of forming longitudinal grooves in the exposed surface of the absorbent material of the insert strip to facilitate moisture distrubution.

7. The method recited in claim 5, wherein the moisture absorbent material is treated with a highly water absorbent starch.

8. A double-duty diaper comprising, in combination, a main diaper including at least one relatively thick substantially rectangular layer of highly moisture absorbent material constituting a longitudinal central portion, a thin layer of moisture impervious material underlying the central portion and extending laterally beyond the longitudinal edges of said central portion, a thin layer of moisture pervious material overlying the central portion and having laterally extending side portions overlying the lateral extensions of the moisture impervious material, said lateral extensions being secured together face to face; and a removable insert strip including a relatively thick body of highly moisture absorbent material of a width responding to the width of and superposed on the said longitudinal central portion of the diaper and of a length greater than the length of said central portion, said thick body having a thin layer of moisture impervious material on its bottom face and a thin layer of moisture absorbing material on its top face, both of said thin layers terminating short of the ends of said thick body and extending laterally beyond the related longitudinal edge of said body, said laterally extending portions of the thin layers being bonded together face to face to form lateral wings, and a rupturable adhesive retaining the insert strip in place on the main diaper.

9. The double-duty diaper recited in claim 8, wherein only the insert strip has a series of longitudinal grooves on its wearer-facing surface to facilitate distribution of moisture.

10. An insert strip for a double-duty diaper comprising a relatively thick strip of moisture absorbent material, a thin layer of moisture impervious material underlying said thick strip, a thin layer of moisture absortive material of substantially the same thickness and size as the first named thin layer overlying said thick strip, said thin layers projecting laterally beyond the longitudinal edges of said thick strip and being of a length shorter than the length of the thick strip, and means bonding the projecting thin layers together face to face to provide foldable wing portions.

11. A double-duty diaper comprising, in combination, a main diaper consisting of a substantially rectangular layer of moisture absorbent material having a longitudinal central portion; and an insert strip including a relatively thick layer of moisture absorptive material, a thin layer of moisture impervious material underlying the thick layer and a thin layer of moisture absorptive material of substantially the same thickness and size as the first named thin layer overlying the thick absorbent layer; said thin layers projecting laterally beyond the longitudinal edges of said thick layer and being of a length less than the length of the thick layer, means bonding the laterally projecting thin layers together face to face to provide foldable wing portion, and adhesive means detachably securing the insert strip to the main diaper.

* * * * *